United States Patent [19]

Atsumi et al.

[11] 4,260,774
[45] Apr. 7, 1981

[54] 5-CARBAMOYL IMIDAZOLES

[75] Inventors: Toshio Atsumi, Ashiya; Yoshiaki Takebayashi, Toyonaka; Yuzo Tarumi, Nishinomiya; Hisao Yamamoto, Kobe, all of Japan

[73] Assignee: Sumitomo Chemical Company, Limited, Japan

[21] Appl. No.: 51,741

[22] Filed: Jun. 25, 1979

Related U.S. Application Data

[63] Continuation-in-part of Ser. No. 30,645, Apr. 16, 1979, abandoned, which is a continuation of Ser. No. 923,404, Jul. 10, 1978, abandoned, which is a continuation-in-part of Ser. No. 811,597, Jun. 30, 1977, abandoned.

[30] Foreign Application Priority Data

Jul. 2, 1976 [JP] Japan .................. 51-79098
Oct. 26, 1976 [JP] Japan .................. 51-12965

[51] Int. Cl.³ .................................. C07D 233/90
[52] U.S. Cl. .................................. 548/336; 548/337; 424/273 R
[58] Field of Search ........................ 548/337, 336; 424/273 R

[56] References Cited

U.S. PATENT DOCUMENTS 4,140,788  2/1979  Atsumi et al. .................. 548/337

FOREIGN PATENT DOCUMENTS 2729865  1/1978  Fed. Rep. of Germany .

OTHER PUBLICATIONS

Hofmann, Imidazole and Its Derivatives, Part I, pp. 8, 26-27, Interscience, New York, 1953.
Remington's Pharmaceutical Sciences, 14th Ed., pp. 1163-1172, Mack Pub. Co., Easton, Pa. 1970.
Usaevich et al. Chemistry of Heterocyclic Cpds., 1973, vol. 7, pp. 746-748, Transl. of Khim, Geterotsikl. Soed. by Consults. Bureau, N. Y.

*Primary Examiner*—Henry R. Jiles
*Assistant Examiner*—Natalia Harkaway
*Attorney, Agent, or Firm*—Wenderoth, Lind & Ponack

[57] ABSTRACT

There are provided compounds of the formula:

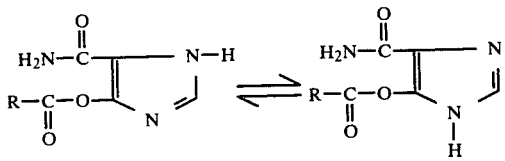

wherein R is an adamantyl group, or a phenyl group unsubstituted or substituted with a lower alkyl group, a lower alkoxy group, a lower alkylthio group, a halogen atom, a nitro group, a cyano group, a methylenedioxy group or an acetamido group, useful as anti-transplanted-tumor agents and immunosuppressants.

15 Claims, No Drawings

5-CARBAMOYL IMIDAZOLES

This is a continuation-in-part of our application Ser. No. 30,645, filed Apr. 16, 1979, now abandoned, which is a continuation of our application Ser. No. 923,404, filed July 10, 1978, now abandoned, which is a continuation-in-part of our application Ser. No. 811,597, filed June 30, 1977, now abandoned.

The present invention relates to novel imidazole derivatives and preparation thereof. More particularly, the present invention pertains to imidazole derivatives useful as antitumor agents and immunosuppressants, and to their preparation and use.

So far, it has been known that bredinin, 4-carbamoyl-1-β-D-ribofuranosylimidazolium-5-olate, has immunosuppressive activity and weak antitumor activity against lymphatic leukemia L1210. [Kimio Mizuno et al. J. of Antibiotics, 27, 775 (1974)]

The aglycone of bredinin, 4-carbamoylimidazolium-5-olate, was also known. [Edgar Shipper et al. J. Amer. Chem. Soc., 74, 350 (1952)] However, the pharmacological properties of 4-carbomoylimidazolium-5-olate were not known till quite recently.

It is reported that growth inhibitory effects on L5178Y cells and immunosuppressive effects are produced by administration of 4-carbamoylimidazolium-5-olate. It is suggested, however, that these effects are not directly produced by it, but they are due to metabolic conversion of 4-carbamoylimidazolium-5-olate to bredinin [Kenzo Sakaguchi et al. J. of Antibiotics, 28, 798 (1975); T. Tsujino et al. Proceedings of the first intersectional congress of IAMS Vol. 3, 441 (1974)]

Imidazole derivatives provided by the present invention are representable by the formula:

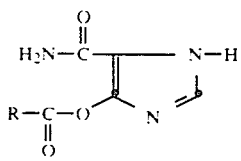

wherein R is an adamantyl group, or a phenyl group unsubstituted or substituted with a lower alkyl group, a lower alkoxy group, a lower alkylthio group, a halogen atom, a nitro group, a cyano group, a methylenedioxy group or an acetamido group.

As used herein, the term "lower alkyl" may preferably include a straight or branched alkyl having 1 to 5 carbon atoms (e.g. methyl, ethyl, n-propyl, isopropyl). The term "lower alkoxy" may preferably include a straight or branched alkoxy having 1 to 5 carbon atoms (e.g. methoxy, ethoxy, n-propoxy, n-butoxy, isobutoxy). The term "lower alkylthio" may preferably include a straight or branched alkylthio having 1 to 5 carbon atoms (e.g. methylthio, ethylthio). The term "halogen" may preferably include fluorine, chlorine, bromine and iodine.

According to the present invention, the imidazole derivatives of the formula:

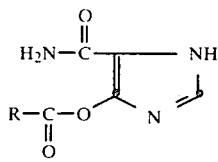

wherein R is as defined above, can be prepared by reacting 4-carbamoylimidazolium-5-olate of the formula:

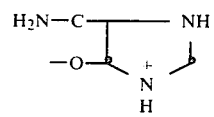

or its silylated derivative with reactive derivatives of carboxylic acids of the formula:

$$RCOOH \qquad (III)$$

wherein R is as defined above.

Examples of preferred reactive derivatives of carboxylic acids of the formula (III) are carboxylic acid anhydrides and halides, preferably chlorides.

The reaction can generally be effected by cooling a reaction mixture at a temperature from 0° to 100° C., preferably for 0° to 60° C. The reaction of 4-carbamoxylimidazolium-5-olate with carboxylic acid halides can usually be carried out in an inert polar solvent or a mixture of water and inert organic solvent preferably in the presence of an inorganic or tertiary organic base. Typical examples of said inert polar solvents are pyridine, dimethylformamide, formamide, dimethylsulfoxide, and dimethylacetamide. Typical examples of said inert organic solvents are ethyl ether, benzene, toluene, chloroform, ethylacetate, n-hexane, and xylene. Examples of preferred inorganic base are sodium hydroxide, sodium carbonate, sodium bicarbonate, potassium carbonate or bicarbonate and potassium hydroxide. Examples of preferred tertiary organic base are triethylamine, N,N-dimethylaniline, and pyridine.

The reaction of 4-carbamoylimidazolium-5-olate with carboxylic acid anhydrides can be carried out in the presence of an inert organic solvent (e.g. methanol, ethanol, dimethylformamide, dimethylsulfoxide, formamide, dimethylacetamide, acetnitrile, acetone, nitromethane, ethyl acetate).

The compounds of the formula (I) can also be prepared by reacting silylated derivative of 4-carbmoylimidazolium-5-olate with aforesaid carboxylic acid halides in an inert organic solvent (e.g. benzene, toluene, xylene, ethylacetate, n-hexane, dichloroethane, anhydrous ethyl ether, anhydrous dioxane, anhydrous tetrahydrofuran).

The reaction can be effected by cooling at a temperature −10° to 30° C., preferably for 1 to 10 hours.

The silylated derivative of 4-carbamoylimidazolium-5-olate are known and can be prepared by known methods. [Hayashi et al. Japanese Patent Kokai 50-121276]4-carbamoylimidazolium-5-olate may exist in the form of the tautomers as follows,

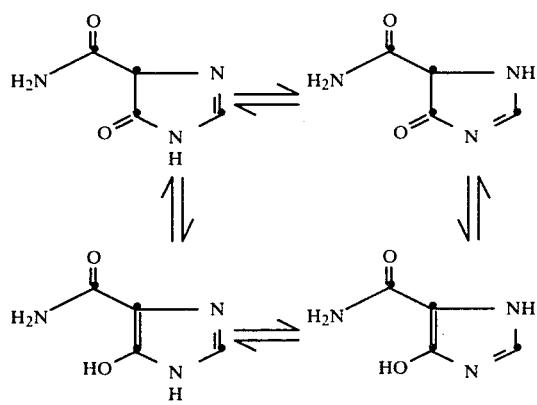

so the position of acylation may be ambiguous.

The compounds of the present invention were incorrectly identified by the formula,

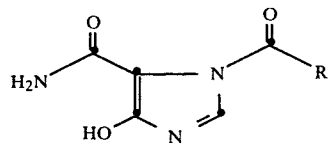

wherein R is as defined above, in our previous application Ser. No. 923,404 though they were correctly identified by the formula:

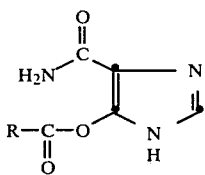

wherein R is as defined above, in our first application Ser. No. 811,597.

Although, in the previous description, the structure of the imidazole derivatives of the present invention is given as represented by the formula (I). The imidazole derivatives of the present invention may exist in a mixture of the two tautomers as follows:

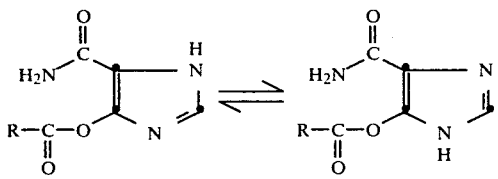

both of which are within the scope of the present invention.

The compounds of the formula (I) possess excellent immunosuppressive activity as well as potent anti-transplanted tumor activity.

For example, they exhibit much higher immunosuppressive activity than those of 6-(1-methyl-4-nitro-5-imidazolyl)mercaptopurine (Azathioprine) and 6-mercaptopurine.

The immunosuppressive activities of the compounds of the present invention, Azathioprine and 6-mercaptopurine are given in the following table. After a sheep red blood cell preparation (SRBC) was injected in mice, the compounds were administered orally once a day on days 0 to 3. The plaque forming cell (PFC) number was measured on day 4 by Cunningham method. [Cunningham A. J. et al. Immunol. 14, 599 (1968)]

TABLE I

| Compounds | Dose mg/kg/day p.o | Effects PFC/spleen $\times 10^{-4}$ | Suppression (%) |
|---|---|---|---|
| 5-Carbamoyl-1H-imidazole-4-yl benzoate | 25 | 19.88 ± 6.06[a] | 68.1 |
|  | 100 | 8.63 ± 2.61[b] | 89.4 |
| 5-Carbamoyl-1H-imidazole-4-yl 1-adamantane carboxylate | 25 | 14.19 ± 2.24[a] | 77.2 |
|  | 100 | 5.19 ± 1.29[b] | 93.6 |
| 5-Carbamoyl-1H-imidazole-4-yl p-chlorobenzoate | 25 | 22.06 ± 5.37[a] | 64.6 |
| 6-Mercaptopurine | 25 | 30.78 ± 6.28 | 60.2 |
| Azathioprine | 100 | 26.73 | 81.6 |
| Control[a] |  | 62.25 ± 11.73 |  |
| Control[b] |  | 81.44 ± 6.56 |  |

The compounds of the present invention have also been found to possess potent antitumor activities against Sarcoma 180, Ehrlich carcinoma, hepatoma MH 134, and P388 leukemia. They exhibit particularly excellent inhibitory effects against solid transplanted tumors.

The antitumor activities of the compounds of the present invention were estimated according to the methods described in "Oyo-Yakuri," Vol. 14, P. 521 (in Japanese).

The results are given in the following Tables II and III.

TABLE II

Antitumor effect on mouse experimental tumors

| Compound | Dosage mg/kg, Route i.p. | Inhibition Ratio (%) Sarcoma 180 (solid) |
|---|---|---|
| 5-Carbamoyl-1H-imidazol-4-yl 1-adamantane-carboxylate | 50 | 53.9 |
|  | 100 | 71.4 |
|  | 200 | 88.8 |
|  | 206 | 100.0 |
| 5-Carbamoyl-1H-imidazol-4-yl p-chlorobenzoate | 100 | 49.1 |
| 5-Carbamoyl-1H-imidazol-4-yl p-fluorobenzoate | 100 | 36.0 |
| 5-Carbamoyl-1H-imidazol-4-yl p-nitrobenzoate | 100 | 44.7 |
| 5-Carbamoyl-1H-imidazol-4-yl 3,4-methylenedioxy-benzoate | 100 | 65.1 |
| 5-Carbamoyl-1H-imidazol-4-yl m-cyanobenzoate | 100 | 38.3 |
| 5-Carbamoyl-1H-imidazol-4-yl p-methylbenzoate | 100 | 38.3 |
| 5-Carbamoyl-1H-imidazol-4-yl p-bromobenzoate | 100 | 66 |
| Mitomycin C | 2 | 74.0 |
| 5-Fluorouracil | 30 | 66.0 |

ICR-JCL male mice, 5 weeks old, weighing between 23 and 26 grams were used. Each test group was composed of 5 mice. One million cells of Sarcoma 180 were injected intramusculary in hind leg. The drug was administered intrapeniteneally at day 1, 3, 5, 7 and 9. After killing the mice at day 10, tumors were removed and weighed. The tumor inhibitory ratio was calculated according to the following formula.

$$IR = \left(1 - \frac{\text{the mean tumor weights of treated group}}{\text{the mean tumor weights of control group}}\right) \times 100$$

TABLE III

| Compound | Antitumor effect on mouse experimental tumor | |
|---|---|---|
| | Dosage mg/kg | Evaluation T/C (%) P388 |
| 5-Carbamoyl-1H-imidazole-4-yl 1-adamantanecarboxylate | 400 | 138 |
| | 200 | 120 |
| | 100 | 112 | animals CDF₁ mouse (6 mice/group)
tumor: mouse leukemia P388
inoculum size: 10⁶ cells/mouse
inoculum site: i.p.
day of administration: day 1 & 5
administration route: i.p.
dose: 100, 200 & 400 mg/kg
evaluation: median survival time The compounds (I) of the present invention have low toxicity. They do not show any toxic symptoms, when over 1000 mg/kg of the compounds are orally administered to a mouse. Moreover, they do not exhibit an influence on decrease of peripheral leucocytes, which is one of the most serious side effects of immunosuppressants.

For the oral or parenteral administration, they are made up alone or together with a conventional pharmaceutical carrier or diluent to a conventional solid or liquid pharmaceutical preparation (e.g. powders, granules, tablets, capsules, suspensions, emulsions, solutions) using the conventional methods in pharmaceutical field.

The following examples are given to illustrate the present invention more precisely but it is not intended to limit the present invention thereto.

EXAMPLE 1

To a suspension of 455 mg of 4-carbamoylimidazolium-5-olate in 5 ml of dry pyridine was added 1.02 g of benzoyl chloride at a temperature below 5° C. After addition was over, the mixture was stirred under ice cooling for 2 hours. Then separated crystals were filtered off, washed with water and ether, dried to give 5-carbamoyl-1H-imidazol-4-yl benzoate, m.p. 204° C. (dec.).

$\nu_{max}^{nujol}$ (cm$^{-1}$; 3450, 3170, 3100 (NH), 1740

EXAMPLE 2

To a suspension of 508 mg of 4-carbamoylimidazolium-5-olate and 486 mg of triethylamine in 6 ml of anhydrous dimethylformamide was added 770 mg of p-chlorobenzoyl chloride in 3 ml of anhydrous dimethylformamide at a temperature below 5° C. The mixture was stirred under ice cooling for 4 hours. The insoluble crystals were filtered off, then the filtrate were concentrated to a residue under reduced pressure, and the resulting residue was dissolved in chloroform. The chloroform solution was washed with water, and dried over anhydrous sodium sulfate. The solvent was removed under reduced pressure to give 5-carbamoyl-1H-imidazol-4-yl p-chlorobenzoate. The crude solid was washed with ethyl acetate to give 340 mg of pure product, m.p. 220° C. (charred).

The following compounds were obtained by substantially the same procedures as described above:

5-Carbamoyl-1H-imidazol-4-yl p-nitrobenzoate
m.p. 177°-184° C. (dec.)

5-Carbamoyl-1H-imidazol-4-yl p-fluorobenzoate
m.p. 214° C. (dec.)

EXAMPLE 3

A mixture of hexamethyldisilazane (10 g), a catalytic amount of ammonium sulfate and 4-carbamoylimidazolium-5-olate (745 mg) was refluxed for an hour and a half. The solution was condensed under reduced pressure to give sililated 4-carbamoylimidazolium-5-olate derivative. The resulting solid (345 mg) was dissolved in dry benzene (30 ml). To the benzene solution was added 350 mg of p-chlorobenzylchloride under ice cooling, then the mixture was stirred for 3 hours and for 6 hours at room temperature. The resulting solution was evaporated in vacuo to dryness and the resulting solid was washed with ethyl acetate to give 5-carbamoyl-1H-imidazol-4-yl p-chlorobenzoate, m.p. 220° C. (charred).

EXAMPLE 4

To a mixture of 1.27 g of 4-carbamoylimidazolium-5-olate in 42.4 g of 10% aqueous solution of sodium carbonate was added 7.38 g of 3,4-methylenedioxybenzoylchloride in 20 ml of toluene at room temperature. After addition was over, the mixture was stirred for 4 hours. Then the separated crystals were filtered off, washed with water and toluene, dried in vacuo to give 5-carbamoyl-1H-imidazol-4-yl 3,4-methylenedioxybenzoate, m.p. 206.5°-208° C. (dec.).

And the following compounds were obtained by the manner similar to that described in Example 4.

5-Carbamoyl-1H-imidazol-4-yl o-methoxybenzoate
m.p. 205° C. (charred).

5-Carbamoyl-1H-imidazol-4-yl m-cyanobenzoate
m.p. 195° C. (dec.).

5-Carbamoyl-1H-imidazol-4-yl p-methylbenzoate
m.p. 211° C. (dec.).

EXAMPLE 5

To a solution of 1-adamantanecarbonylchloride (39.73 g) in pyridine (260 ml) was added 4-carbamoylimidazolium-5-olate (12.71 g) and the reaction temperature was maintained at 41°-43° C. for 3.5 hours. Pyridine was removed under reduced pressure. To the residue was added ethylacetate (300 ml) and water (300 ml), and stirred at room temperature for 1 hour. The insoluble solid was filtered and washed with ethyl acetate to give almost pure 5-carbamoyl-1H-imidazol-4-yl 1-adamantanecarboxylate (25.9 g, β form, m.p. 205°-205.5° C. (dec.)). Recrystallization from dimethylformamide-diethylether gave analytically pure sample (β form m.p. 213.5°-216.5° C. (dec.)).

Elemental analysis:
Calculated for $C_{15}H_{19}O_3N_3 = 289.33$

| | C: 62.26%, | H: 6.62%, | N: 14.52% |
|---|---|---|---|
| Found | C: 62.5%, | H: 6.7%, | N: 14.7% |

EXAMPLE 6

To a suspension of 4-carbamoylimidazolium-5-olate (1.016 g) in dimethylformamide (20 ml) was added triethylamine (1.942 g) at 0°–5° C. and then 1-adamantanecarbonylchloride (3.50 g) in dimethylformamide (20 ml) dropwisely over 24 minutes. The reaction mixture was stirred at 0°–5° C. for 23 hours. The solvent was removed under reduced pressure. To the residue was added ethyl acetate (20 ml) and water (20 ml), and stirred at room temperature for 1 hour. The insoluble solid was filtered and washed with ethyl acetate to give almost pure 5-carbamoyl-1H-imidazol-4-yl 1-adamantanecarboxylate (1.5 g, α form, m.p. 206.5°–207.5° C. (dec.)), which was washed thoroughly with ethyl acetate to give pure product, α form, m.p. 211° C. (dec.).

EXAMPLE 7

To a solution of 1-adamantanecarbonylchloride (2.980 g) in pyridine (26 ml) was added 4-carbamoylimidazolium-5-olate (1.271 g) and the reaction temperature was kept at 40°–43° C. for 4 hours. Unreacted starting material was recovered by filtration (210 mg). The filtrate was concentrated under reduced pressure. To the residue was added ethyl acetate (30 ml) and water (30 ml), and stirred at room temperature for 1 hour. The insoluble solid was filtered and washed with ethyl acetate to give almost pure 5-carbamoyl-1H-imidazol-4-yl 1-adamantanecarboxylate (1.602 g, α form, m.p. 207°–209° C. (dec.)).

EXAMPLE 8

To a suspension of 4-carbamoylimidazolium-5-olate (1.271 g) in pyridine (16 ml) was added dropwisely 1-adamantanecarbonylchloride (4.371 g) in dimethylformamide (28 ml) over 17 minutes. The reaction mixture was stirred at 65°–67° C. for 6 hours and then concentrated under reduced pressure. To the residue was added ethyl acetate (30 ml) and water (30 ml), and stirred at room temperature for 1 hour. The insoluble solid was filtered and washed with ethyl acetate to give 5-carbomoyl-1H-imidazol-4-yl 1-adamantanecarboxylate (1.372 g, α form, m.p. 207°–208° C. (dec.)). Additional product (0.335 g, β form, m.p. 205°–208° C. (dec.)) was obtained from the organic layer of the filtrate after the operation mentioned above.

EXAMPLE 9

To a suspension of 4-carbamoylimidazolium-5-olate (4.064 g) in dimethylformamide (80 ml) was added triethylamine (7.768 g) at 0°–5° C. and then 1-adamantanecarbonylchloride (14.00 g) in dimethylformamide (80 ml) dropwisely over 22 minutes. The reaction mixture was stirred at 0°–5° C. for 15 hours. The solvent was removed under reduced pressure. To the residue was added ethyl acetate (100 ml) and water (100 ml), and stirred at room temperature for 1 hours. The insoluble solid was filtered and washed with ethyl acetate to give almost pure 5-carbamoyl-1H-imidazol-4-yl 1-adamantanecarboxylate (5.67 g, β form, m.p. 207°–210° C. (dec.)).

EXAMPLE 10

To a suspension of 5.084 g of 4-carbamoyl-imidazolium-5-olate in 104 ml of dry pyridine was added 11.41 g of p-bromobenzoyl chloride at room temperature. After addition was over, the mixture was stirred at 40°–45° C. for 2.5 hours. The separated crystals were filtered off, washed with chloroform and diisopropyl ether, dried under vacuum to give 10.535 g of 5-carbamoyl-1H-imidazol-4-yl p-bromobenzoate, m.p. 232°–233° C. (dec.)

Elemental analysis:
Calculated for $C_{11}H_8N_3O_3Br$ (310.10):

|  | C | H | N | Br |
|---|---|---|---|---|
|  | 42.60% | 2.60% | 13.55% | 25.77% |
| Found: | 42.6% | 2.5% | 13.8% | 25.76% |

EXAMPLE 11

To a suspension of 636 mg of 4-carbamoylimidazolium-5-olate in 15 ml of dry pyridine was dropwisely added 1.0 g of o-methylbenzoyl chloride at less than 5° C. in $N_2$ atmosphere. After being stirred for 2 hours at 41°–43° C., the reaction mixture was cooled to room temperature and 658 mg of triethylamine was added. Then the reaction mixture was concentrated under reduced pressure. To the residue was added chloroform (about 20 ml) and then separated crystals were filtered off, washed with chloroform, toluene and ether, and dried to give 600 mg of 5-carbamoyl-1H-imidazol-4-yl o-methyl benzoate, m.p. 181.5°–182.5° C.

Recrystallized was 447 mg of crude material from N,N-dimethylformamide and water.
Amount: 416 mg.
m.p.: 185°–185.5° C. (dec.)
$\nu_{max}^{nujol}$ (cm$^{-1}$): 3460, 3170, 1740, 1675, 1610, 1470, 1435, 1255, 735.

Elemental analysis:
Calculated for $C_{12}H_{11}O_3N_3 \cdot O.3H_2O$

|  | C | H | N |
|---|---|---|---|
|  | 57.50% | 4.66% | 16.76% |
| Found: | 57.48% | 4.34% | 16.91% |

The following compound was obtained in the same manner as described above.

1.258 g of 5-carbamoyl-1H-imidazol-4-yl p-methylthiobenzoate was synthesized from 0.636 g of 4-carbamoylimidazolium-5 olate and 1.4 g of p-methylthiobenzoyl chloride.
m.p. 219° C. (charred)

Recrystallized was 512 mg of crude material from N,N-dimethylformamide and water.
Amount: 495 mg.
m.p.: 219° C. (charred)
$\nu_{max}^{nujol}$ (cm$^{-1}$): 3440, 1725, 1665, 1600, 1590, 1460, 1370, 1270.

Elemental analysis:
Calculated for $C_{12}H_{11}N_3O_3S$:

|  | C | H | N |
|---|---|---|---|
|  | 51.98% | 4.00% | 15.15% |
| Found: | 52.0% | 3.7% | 15.0% |

0.255 g of 5-carbamoyl-1H-imidazol-4-yl o-chlorobenzoate was synthesized from 0.524 g of 4-carbamoylimidazolium-5 olate and 0.952 g of o-chlorobenzoyl chloride,
m.p. 144.5°–147.5° C. (dec.)
$\nu_{max}^{nujol}$ (cm$^{-1}$): 3460, 3420, 3150, 1750, 1660, 1590, 1450, 1370, 1230, 1010, 730

Elemental analysis:
Calculated for $C_{11}H_8N_3O_3Cl \cdot 1H_2O$:

|       | C      | H     | N     | Cl     |
|-------|--------|-------|-------|--------|
|       | 46.58% | 3.55% | 14.8% | 12.50% |
| Found: | 46.7% | 3.6%  | 15.3% | 12.83% |

According to the present invention, there are obtained, for example, the following compounds:
5-Carbamoyl-1H-imidazol-4-yl m-chlorobenzoate,
5-Carbomoyl-1H-imidazol-4-yl p-acetamidobenzoate,
5-Carbamoyl-1H-imidazol-4-yl o-fluorobenzoate,
5-Carbamoyl-1H-imidazol-4-yl m-fluorobenzoate,
5-Carbamoyl-1H-imidazol-4-yl m-nitrobenzoate,
5-Carbamoyl-1H-imidazol-4-yl o-nitrobenzoate.

What is claimed is:
1. A compound of the formula

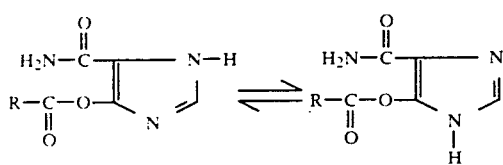

wherein R is an adamantyl group, or a phenyl group unsubstituted or substituted with a lower alkyl group, a lower alkoxy group, a lower alkylthio group, a halogen atom, a nitro group, a cyano group, a methylenedioxy group or an acetamido group.

2. A compound according to claim 1, wherein R is a phenyl group substituted with a lower alkyl group, a lower alkoxy group, a lower alkylthio group, a halogen atom, a nitro group, a cyano group, a methylenedioxy group, or an acetamido group.

3. A compound according to claim 1, wherein R is adamantyl.

4. A compound according to claim 1, wherein R is phenyl.

5. A compound according to claim 2, wherein R is p-chlorophenyl.

6. A compound according to claim 2, wherein R is 3,4-methylenedioxyphenyl.

7. A compound according to claim 2, wherein R is p-nitrophenyl.

8. A compound according to claim 2, wherein R is parafluorophenyl.

9. A compound according to claim 2, wherein R is o-methoxyphenyl.

10. A compound according to claim 2, wherein R is m-cyanophenyl.

11. A compound according to claim 2, wherein R is p-tolyl.

12. A compound according to claim 2 wherein R is p-bromophenyl.

13. A compound according to claim 2, wherein R is o-tolyl.

14. A compound according to claim 2, wherein R is p-methylthiophenyl.

15. A compound according to claim 2, wherein R is p-chlorophenyl.

* * * * *